US00PP15816P2

(12) United States Plant Patent
Kawashima

(10) Patent No.: US PP15,816 P2
(45) Date of Patent: Jun. 28, 2005

(54) ***OSTEOSPERMUM* PLANT NAMED 'KAKEGAWA AU12'**

(50) Latin Name: *Osteospermum hybrida*
Varietal Denomination: Kakegawa AU12

(75) Inventor: Moriya Kawashima, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 120 days.

(21) Appl. No.: 10/775,615

(22) Filed: Feb. 10, 2004

(51) Int. Cl.[7] ..... A01H 5/00
(52) U.S. Cl. ..... Plt./360
(58) Field of Search ..... Plt./360

(56) References Cited

PUBLICATIONS

Proven Winners: *Osteospermum* hybrids. Elsner pac Jungpflanzen GbR [online], [retrieved on Jun. 15, 2004]. Retrived from the Internet <http://www.pac–elsner.com/uk/proven–winners/proven–index.htm>.*

* cited by examiner

*Primary Examiner*—Anne Marie Grunberg
*Assistant Examiner*—June Hwu
(74) *Attorney, Agent, or Firm*—Jondle & Associates P.C.

(57) ABSTRACT

An *Osteospermum* cultivar particularly distinguished by its yellow flower color and tendency to hold flowers open later in the evening.

1 Drawing Sheet

Genus and species: *Osteospermum hybrida.*
Variety denomination: 'Kakegawa AU12'.

BACKGROUND OF THE NEW PLANT

The variety 'Kakegawa AU12' originated from a cross made in March 2001 in Misato, Japan. The female parent was a tetraploid *Osteospermum* sp. developed using the variety 'Seikilrem' (U.S. Plant Pat. No. 13,407). The male parent was an unnamed *Dimorphotheca sinuate* with small, yellow flowers, shiny petals, long internodes and prostrate habit. Seed from this cross was sown in June 2001 and plants were transplanted to the outdoor field. In October 2001, single-plant selections were made for vegetative propagation using plant habit and flower color as selection criteria. One selection, designated breeder code M2-123, became the new variety 'Kakegawa AU12'. The traits of 'Kakegawa AU12' were found to be reproducible, stable and true to type in successive generations of asexual propagation.

DESCRIPTION OF PHOTOGRAPHS

This new *Osteospermum* plant is illustrated by the accompanying photographs which show blooms and foliage of the plant in full color. The colors shown are as true as can be reasonably obtained by conventional photographic procedures.

DESCRIPTION OF THE NEW CULTIVAR

Figure 1:
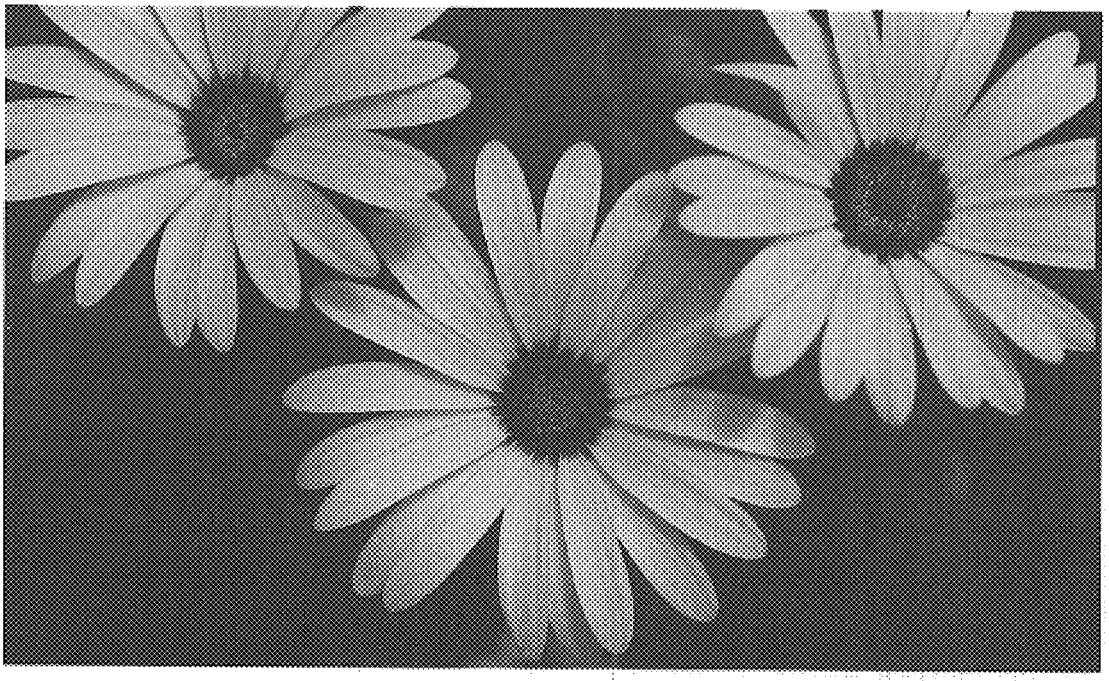
FIG. 1 shows a close-up view of several inflorescences.
Figure 2:
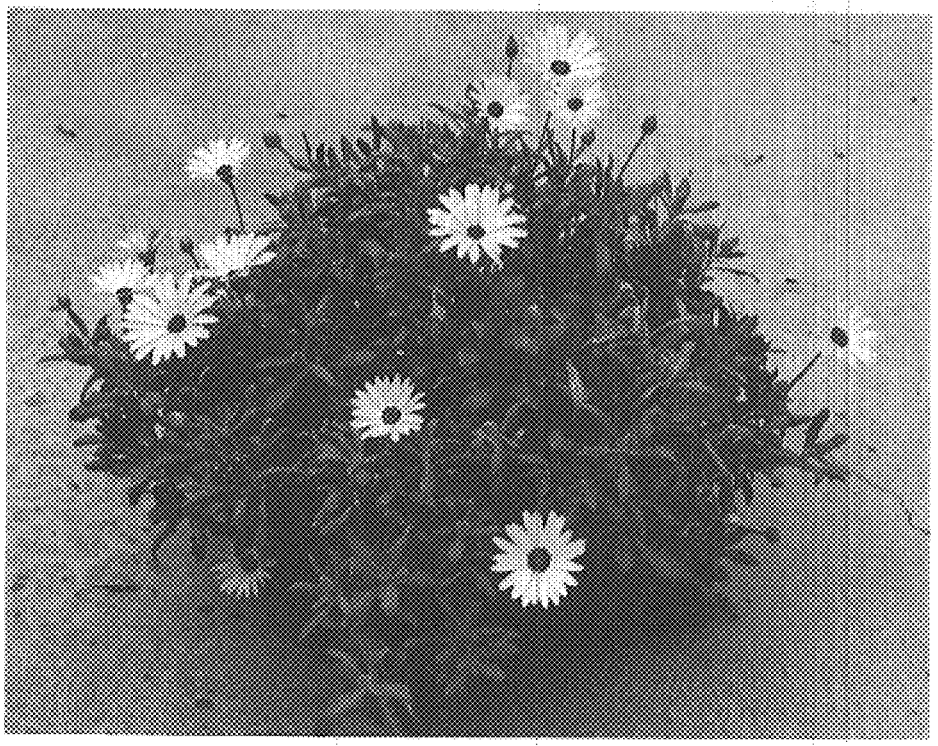
FIG. 2 shows the entire plant, including flower buds, open blooms and foliage.

The following detailed descriptions set forth the distinctive characteristics of 'Kakegawa AU12'. The data which defines these characteristics were collected from asexual reproductions carried out in Salinas, Calif. Data was collected on plants 20 weeks from transplanting rooted cuttings into 16 cm diameter pots, one plant per pot. Color references are to The R.H.S. Colour Chart of The Royal Horticultural Society of London (R.H.S.).

DESCRIPTION OF THE NEW PLANT

Classification:
Family: Compositae.
Botanical: *Osteospermum hybrida.*
Parentage:
- *Female parent.*—Breeding line 'Seikilrem' (U.S. Plant Pat. No. 13,407).
- *Male parent.*—Breeding line *Dimorphotheca sinuate* (unnamed).

Growth:
- *Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of Dip 'N Grow root inducing solution in water. The trays are misted hourly during rooting.
- *Environmental conditions for plant growth.*—Rooted cuttings are transplanted to pots with a 16 cm diameter, one plant per pot. Peat moss-based growing media is used. The pots are watered using a 150–200 ppm fertilizer solution containing 18% nitrogen, 8% phosphorus and 18% potassium. The soil is allowed to dry between waterings. During the first few weeks after transplanting the plants should have evening temperatures around 15–18° C. for good root growth. When plants reach 7.5–10 cm in height they are pinched back to 5–6 leaves to promote branching. Spring and summer daytime high temperatures in Salinas, Calif., where the data was collected, range from 16–25° C.
- *Time to bloom from propagation.*—Approximately four weeks when rooted vegetative cuttings are transferred to a 16 cm. diameter pot. Flowering season is all year in the United States. Vernalization is not required to induce flowering.

*Habit.*—Mounding.
*Life cycle.*—Perennial.

Plant:
*Form.*—Low growing, open branching.
*Plant size.*—Height is 25–40 cm; width 35–50 cm.

Stems:
*Internode length.*—0.5–2.0 cm.
*Stem color.*—Yellow-green (RHS N144A).
*Stem description.*—Ancipital.
*Stem diameter.*—4.0–5.0 mm.
*Pubescence.*—Slight.
*Pubescence shape.*—Linear.
*Pubescence color.*—White (RHS N155A).

Leaves:
*Arrangement.*—Alternate.
*Shape.*—Oblanceolate.
*Apex.*—Mucronate.
*Base.*—Decurrent.
*Margin.*—Serrate.
*Venation.*—Pinnate.
*Surface.*—Dull, smooth.
*Surface pubescence.*—Slight, white (RHS N155A).
*Length.*—4.0–6.5 cm.
*Width.*—1.2–1.5 cm.
*Thickness.*—1.0 mm.
*Color.*—Upper is green (RHS 137A); Lower is green (RHS 137A).
*Venation color.*—Upper is green (RHS 137C); Lower is green (RHS 137C).

Inflorescence:
*Type.*—Capitulum (head); disc florets are perfect and ray florets are carpellate.
*Diameter.*—5.5–7.0 cm.
*Depth.*—2.5–3.0 cm.
*Petal numbers.*—20–24.
*Disc diameter.*—1.0–1.2 cm.
*Disc floret number.*—105–110.
*Flowering habit.*—Determinate.
*Flowers life span.*—3–4 days.
*Fragrance.*—None.
*Seed production.*—None.
*Peduncle length.*—5.0–9.0 cm.
*Peduncle diameter.*—2.0–3.0 mm.
*Peduncle color.*—Yellow-green (RHS 146B).
*Peduncle texture.*—Pubescence.
*Phyllaries.*—20–24 per inflorescence, free, arranged symmetrically; Length — 1.3–1.5 cm; Width — 2.0–3.0 mm; Apex — Acute; Margin — Entire; Shape — Linear, acute; Color — Upper, green (RHS 141B); Lower, green (RHS 143A).

Ray florets:
*Corolla.*—One petal per ray floret. Only the outer row of florets are the ray florets.
*Petals length.*—3.6–3.7 cm.
*Petal width.*—0.6–0.8 cm.
*Petal shape.*—Spatulate.
*Petal apex.*—Acute.
*Petal margin.*—Entire.
*Petal color.*—Upper, yellow (RHS 11A) with base violet-blue (RHS 96A); Lower, yellow (RHS 12A) with base yellow-green (RHS 150D).
*Petal pubescence.*—Glabrous.
*Ovary.*—Superior.
*Pistil length.*—0.8–0.9 cm.
*Stigma form.*—One style with two stigma branches.
*Stigma color.*—Blue (RHS 103A).
*Style color.*—White (RHS N155A).

Disk florets:
*Bud color.*—Green (RHS 137C).
*Bud shape.*—Tubular.
*Bud apex.*—Rounded.
*Bud surface.*—Pubescent.
*Bud size.*—Length 1.4–1.6 cm; width 1.0 mm.
*Pistil form.*—One style with two stigma branches.
*Ovary.*—Superior.
*Style color.*—White (RHS N155A).
*Stigma color.*—Blue (RHS 103A).
*Stamens.*—5, fused into a single tube.
*Anther color.*—Purple (RHS 103A).
*Pollen color.*—Yellow-orange (RHS 23A).

DISEASE AND INSECT RESISTANCE

Plants are susceptible to aphids, thrips, whiteflies and worms.

COMPARISON WITH KNOWN CULTIVARS

'Kakegawa AU12' is most similar to the variety 'Seikilrem' (U.S. Plant Pat. No. 13,407). The two plants differ in leaf size, pollen color and flower petal colors. For 'Kakegawa AU12,' petals are medium yellow in color with a small area of violet-blue at the base of the petal. The two color areas are very distinct and have no fading. The petals of of 'Seikilrem' are lighter yellow and have a darker violet-blue base. The petal base color tends to fade into the yellow found on the upper portion of the petal. The following Table 1 compares the differences between the two plants.

TABLE 1

| Trait | 'Kakegawa AU12' | 'Seikilrem' |
|---|---|---|
| Petals | Yellow (RHS 11A) petals with solid base of violet-blue (RHS 96A) | Yellow (RHS 11B) petals with violet-blue (RHS N92B) at the base |
| Leaf Size | Length: 4.0–6.5 cm<br>Width: 1.2–1.6 cm | Length: 3.0–4.0 cm<br>Width: 0.8–1.2 cm |
| Pollen color | Orange (RHS 23A) | Orange (RHS 25B) |

I claim:

1. A new and distinct cultivar of *Osteospermum* plant as shown and described herein.

* * * * *